United States Patent [19]
Nilsson

[11] Patent Number: 6,077,695
[45] Date of Patent: Jun. 20, 2000

[54] METHOD OF PRODUCING DERIVATIVES OF GLC-β 1-4GLC-N-ACETYL

[75] Inventor: Kurt G. I. Nilsson, Lund, Sweden

[73] Assignee: Bioflexin AB, Lund, Sweden

[21] Appl. No.: 08/981,715

[22] PCT Filed: Jul. 13, 1995

[86] PCT No.: PCT/IB95/00561

§ 371 Date: Jun. 16, 1998

§ 102(e) Date: Jun. 16, 1998

[87] PCT Pub. No.: WO97/03206

PCT Pub. Date: Jan. 30, 1997

[51] Int. Cl.$^7$ .............................. C12P 19/26; C12N 9/42; C12N 9/24
[52] U.S. Cl. ........................... 435/84; 435/200; 435/209; 435/255.1
[58] Field of Search .............................. 435/84, 200, 209, 435/255.1

[56] References Cited

FOREIGN PATENT DOCUMENTS

89/09275 10/1989 WIPO .
93/03168 2/1993 WIPO .

OTHER PUBLICATIONS

Measurement of Interhelical Electrostatic Interactions in the GCN4 Leucine Zipper, Lumb et al. Science, vol. 268, Apr. 21, 1995, pp. 432–435.

Carbohydrate Structure of Human Fibrinogen, The Journal of Biological Chemistry, vol. 257, No. 16, Issue of Aug. 25, 1982, pp. 9704–9710.

Asymmetric Synthesis of Complex Oligosaccharides, Kurt Nilsson, pp. 130–139, in Copping, L. (ed), "Opportunities in Biotransformation" London (1990).

*Primary Examiner*—Rebecca E. Prouty
*Attorney, Agent, or Firm*—Smith Gambrell & Russell, LLP.

[57] ABSTRACT

Disclosed is a method of producing a compound which contains the Glcβ1-4GlcN structure involving reacting at least one donor substance GlcβOR where R is an organic group, and at least one acceptor substance which is a glucopyranosamino derivative having the formula GlcNR"-R'", wherein NR" is an azido, 2-N-acetyl-, 2-N-phtalimido, or an organic group bound to the 2-N-group of glucosamine, wherein R'" is a glycosidically bound fluoro or is an O-, C-, N- or S-glycosidically bound aliphatic or aromatic compound, with the optional proviso that if NR" is NHAc then R'" is not OH and if NR" is not NHAc then R'" may be OH, in the presence of *Bullera singularis* or an E.C. group 3.2 glycosidase of essentially the same structure as an E.C. group 3.2 glucosidase obtained from *Bullera singularis* to form the Glcβ1-4GlcN derivative; and optionally isolating the compound which contains the Glcβ1-4GlcN structure.

24 Claims, No Drawings

METHOD OF PRODUCING DERIVATIVES OF GLC-β 1-4GLC-N-ACETYL

INTRODUCTION AND BACKGROUND

The present invention describes a new method for the production of certain carbohydrate containing compounds related to glycosaminoglycans and glycoconjugates; namely, Glcβ1-4GlcNAc, derivatives thereof and substances derived therefrom. In a further aspect the present invention relates to products produced by the above method as well as uses of the resulting products.

Glycoconjugates contain saccharide chains with from one up to twenty monosaccharide units and in which certain sequences have been shown to have biological activity, for example in the binding of different cells, pathogens, toxins, as well as antibodies or other proteins to cell surfaces, in cancer metastasis, in inflammatory processes, for instance selectin-carbohydrate interactions in the binding of white blood cells to the blood vessel wall, as a modifier of the biological activity and stability of glycoproteins, as immunogenic substances, which have potential in the vaccination against different diseases (See for instance Annual Review of Biochemistry, vol. 58 (1989), pages 309–350, and Current Opinion in Structural Biology, for example review articles in vol. 3 (1993) and references therein).

Structures containing the sequence Galβ1-4GlcNAc, called N-acetyl-lactosamine below, are especially of importance and are found for instance in glycoconjugate oligosaccharides of the lactosamine type. The structure is found in blood group structures, for instance Lewis-x (e.g. Galβ1-4 (Fucα1-3)GlcNAc), sialylated Lewis-x and 3'-sulfated Lewis-x, and is of importance in e.g. selectin-carbohydrate interactions (as reviewed by J. B. Lowe, in Molecular Glycobiology, pages 163–205, Fukuda and Hindsgaul, Eds., IRL Press at Oxford University Press, Oxford, 1994; see also Curr. Opin. Struct. Biol. vol. 3 (1993)).

Glycosaminoglycans such as heparin and smaller fragments thereof have been shown to have biological activity, for example in the binding of different cells, pathogens, toxins, as well as antibodies or other proteins to cell surfaces, in cancer metastasis, in inflammatory processes (See for instance Annual Review of Biochemistry, vol. 58 (1989), pages 309–350, and Current Opinion in Structural Biology, for example review articles in vol. 3 (1993) and references therein; Science (1995), volume 268, pages 432–435).

Structures containing the disaccharide unit GlcAβ1-4GlcN, see structures below, are especially of importance and are found for instance in heparin (see e.g., Curr. Opin. Struct. Biol. vol. 3 (1993); Science (1995), volume 268, pages 432–435).

It is of interest to be able to produce derivatives of GlcAβ1-4GlcN in large quantities for biological/clinical studies/tests, for example for inhibition or modification of the selectin-carbohydrate interaction in vivo to inhibit/modify cell-mediated inflammatory processes (for instance in acute septic shock, ARDS, reperfusion injuries, rheumatoid arthritis, virus-induced pneumonia, psoriasis and the like).

Chemical methods known heretofore to produce GlcAβ1-4GlcN and derivatives thereof have demanded multi-step synthesis and are often expensive and labor intensive.

SUMMARY OF THE INVENTION

The present invention describes a method which with unexpectedly high specificity gives the β1-4 linkage in the synthesis of different Glcβ1-4GlcN derivatives, using abundant donor substances such as cellobiose and other low cost glucosyl donor substances. In one embodiment of the invention, the method is carried out by using the yeast *Bullera singularis* as a catalyst (classified as *Bullera singularis* according to Yeasts, second edition by Barnett et al., Cambridge University Press, 1990).

In a second embodiment, the process of the invention is carried out by using enzymes (which belongs to the group of glycosidases, EC Group 3.2), preferably in a crude, partially isolated or isolated form, especially β-glycosidase or β-glucosidase from *Bullera singularis* but also other β-glucosidase e.g. recombinant, of the same structure or of a similar structure (e.g., containing similar active site structure) as the one from *Bullera singularis*.

DETAILED DESCRIPTION OF THE INVENTION

According to the more detailed aspects of the present invention, the process for producing Glcβ1-4GlcNAc derivatives can be carried out as an equilibrium (reversed hydrolysis) reaction or preferably as a kinetic (transglycosylation) reaction. As is known in the art, the principles of an equilibrium reaction and a kinetic reaction are well understood (e.g. see K. G. I. Nilsson, Trends in Biotechnol. (1988), pages 256–264).

In the case where the reaction is carried out as a transglycosylation reaction, the glycosyl donor is a glycoside, e.g. of D-glucose (Glc) modified in the C-1 position (anomeric position) but it can also be an oligosaccharide, such as cellobiose (Glcβ1-4Glc or aglycoside thereof, e.g.:

R can be a glycosidically linked organic group, for example sugar (e.g. $C_nH_{2n}O_n$ or $C_nH_{2n-2}O_{n-1}$ such as glucose), lower alkyl group (e.g. —Me, —Et) or an aromatic group (e.g. phenyl (—Ph), umberriferyl or m-, o-, or p-nitrophenyl group), preferably R is Glc (glucose) or nitrophenyl. Other glycosides (e.g. F-, N- or S-glycosides) may be selected.

It is known in the art that glycosidases allow some modification of the glycon part (i.e., the glucosyl part in the present invention) of the glycosyl donor. Therefore, in addition to GlcβOR, donors where the glucosyl part have been partially modified in a way still allowing the transglycosylation reaction to occur, resulting in the β1-4 linkage between the glycon part of the glycosyl donor and the glucosamine derivative, can be selected by the person skilled in the art for use with the method according to the present invention. Examples of such modifications of the glycon are modifications where one of the hydroxyl groups of Gal has been modified or substituted for by an inorganic (e.g. —F, —H) or an organic group, e.g. a lower alkyl (e.g. methyl), allyl or an acetyl group. The selection of such a donor in the method according to the invention thus gives a β1-4 linked product in which the glucosyl part is correspondingly modified. Products of the type R'-Glcβ1-4GlcNR''-R''' may thus be prepared where R'-Glc relates to a modified glycon of the glycosyl donor. In the case of a transglycosylation reaction, the glycosyl donor in the scheme shown below, R'-Glc-R, is a β-glycoside:

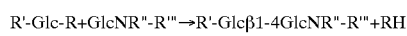

In the transglycosylation reaction, GlcβOR+GlcNR''-R'''→Glcβ1-4GlcNR''-R'''+ROH the reaction rate is higher than in the equilibrium reaction since the glycoside or disaccharide is more reactive than the non-activated sugar D-glucose used as donor in the equilibrium reaction. An enzyme of less purity, even a non-purified enzyme, can be used in the reaction since the enzymes are substrate/linkage specific and contaminating enzymes (e.g., α-glucosidase) will not react with GlcβOR to give a β-linked product. Thus, intact cells (e.g. yeast) can be used as well as partially purified enzyme or enzyme of higher purity.

Hydrolysis of GlcβOR will also occur to a certain extent depending on the reaction conditions. Lower or higher temperatures (e.g., room temperature or higher, e.g. 25°–65° C.) can be selected, organic (co)solvents (acetone, acetonitrile, tetrahydrofurane) can be used, the pH typically is selected from the range 4 to 8, the substrate concentrations are typically 30 mM to several M concentration (e.g. 7 M) depending on the solubility of the substrates, stability of substrate and enzyme in the reaction mixture, and the particular goal of the reaction and the type of substrates.

The reaction will go through a maximum of product formation and has to be followed (e.g., preferably by HPLC) and terminated after an appropriate time by e.g. heat treatment at e.g. 80°–100° C. for e.g. three minutes. Generally, donor consumption is tracked and the reaction terminated after a suitable time, which depends on the conditions, and often at ≧40% consumption of the donor. The reaction can be carried out for a few minutes to several hours depending on the growth of yeast cells (if fermentation conditions are used), the amount of enzyme, temperature, pH, concentration of substrates, and other factors.

The reaction can be monitored by means of TLC, HPLC or by spectrophotometric measurement of liberated aglycon (e.g. nitrophenol, 400 nm). Charring of TLC plates with sulfuric acid may be used for detection of sugars. When a desired yield of the product has been obtained, the reaction is terminated by denaturation of the enzyme by for example heat treatment. Heating to 85° C. or above for 3–5 min (eventually followed by addition of ethanol to a concentration of about 80%) is usually sufficient. If immobilized enzyme is used, the reaction may be terminated by centrifugation or filtration.

In each type of reaction depicted above, N-acetyl-D-glucosamine or a D-glucopyranosamino derivative is used as acceptor (GlcNR"-R"') where R" and R"' are defined below.

In the case of N-acetyl-glucosamine (R"=-HAc group in the 2 position, i.e. in the N-position of 2-glucosamine; the 2-position in glucosamine contain a -NHAc), R"' represents an aglycon other than the anomeric hydroxyl group (i.e. R"' is not OH) or optionally R"' is a hydroxyl group. If R" is not a HAc group then R"' can be OH but can also represent a modification of the anomeric hydroxyl group as in the case where R" is -HAc.

The method according to the invention can be used to produce Glcβ1-4GlcNR"-R"' in high purity (no other linkages observed by 400 MHZ NMR), a product which after isolation can be used for biological/therapeutical purposes or for further synthesis according to the invention. The method can also be used to produce Glcβ1-4Glcβ1-4GlcNR"-R"'. Thus, with the same enzyme and in a further reaction one will obtain Glcβ1-4Glcβ1-4GlcNR"-R"' as shown by the following equation:

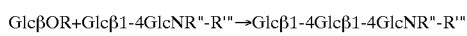

GlcNR"-R"', (the derivative of glucosamine which is used as acceptor), is of the general structure shown in the example below:

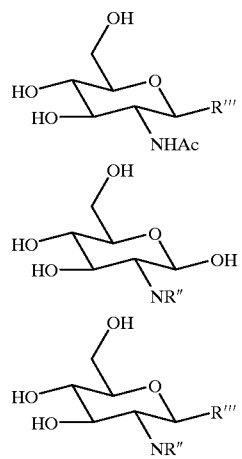

where NR" may be selected from compounds containing an inorganic group (e.g. $N_3$, $NHSO_3H$) and/or an organic group bound to the 2 position of glucosamine, such as (a) N-phthalimido; (b) an organic carbonyl group NH—C(O)—R where R is a hydrogen or a compound containing an organic group, e.g. aliphatics such as alkyl (e.g. methyl, ethyl, propyl), alkoxy (e.g. methoxy, ethoxy), allyloxy, amino acid or polypeptidyl residue, and/or aromatics such as phenyl, benzyl or phenyloxy, preferred examples include N-chloromethoxyacetyl, N-phenoxyacetyl, NHBoc (Boc=t-butyloxycarbonyl), NHAc and $NHC(O)(CH_2)_nCH_3$ (n is an integer equal to or greater than 1); (c) NHR where R is a compound containing an aliphatic and/or aromatic group as described above, for example lower alkyl, preferred examples include $NH(CH_2)_nCH_3$ (n is an integer equal to or greater than 1); or (d) NRR' where R and R' are independently selected from compounds containing an aliphatic and/or aromatic group as described above; preferably NR" is azido, 2-N-acetyl-, or 2-N-phthalimido;

and where R"' is selected from a glycosidically bound inorganic compound, e.g. fluoro or is selected from an O-, C-, N- or S-glycosidically bound compound containing an aliphatic and/or aromatic group, for example lower alkoxy (e.g. methyloxy (-OMe), ethyloxy (-OEt)), lower thioalkyl (e.g. β-linked thioethyl (-SEt)), thioaromatic (e.g. thiophenyl-), -OEtBr, nitrophenoxy, amino acid, peptide, or derivative thereof, or another organic group of interest for the use of the product, or R"' can be —OH if NR" is not NHAc but R"' is not —OH if NR" is NHAc.

The Glcβ1-4GlcN containing product obtained with GlcβOR as donor in the method according to the present invention is of the general structure shown in the example below:

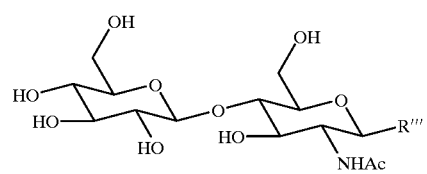

Abbreviation:
Glcβ1-4GlcNAc-R"'

-continued

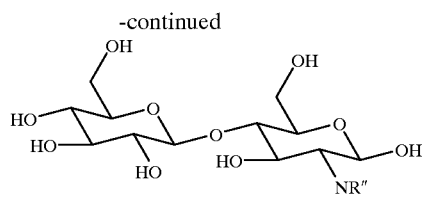

Abbreviation:
Glcβ1-4GlcNR″-R‴

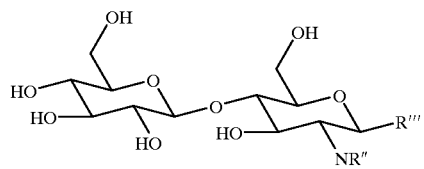

Abbreviation:
Glcβ1-4GlcNR″-R‴

Such conjugates where Glcβ1-4GlcN containing structure, or higher oligosaccharides containing the above structure, is N- or O-glycosidically bound to organic groups, or to amino acids or peptide sequences, via the glucosamine residue and derivatives thereof as described above, are of interest to produce synthetically for fundamental studies and for synthesis of biologically/medically active fragments or analogs of glycoproteins or glucosaminoglycans, for instance to be used as vaccine or therapeutics. It is also important to be able to synthesize oligosaccharide analogues/derivatives of the structures above and according to the present invention to modify or improve the biological activity of the conjugate.

The synthetic procedure according to the invention can is be carried out under highly diverse conditions in regards to, for example, pH, type of buffer, temperature and concentration of the reactants. Various cosolvents (N,N-dimethyl formamide, acetonitrile, dimethyl sulfoxide, dioxane, pyridine, methanol, ethanol, ethylene glycol, etc.) may be used and in varying concentrations together with water. In general, hydrophobic acceptor substances are more easily dissolved by the use of organic cosolvents or increased temperature. Moreover, the reactions may be carried out in two-phase systems, e.g. water-organic solvent or in two-phase systems of water-water polymer. The use of acceptors modified with organic groups facilitates recovery of the product in the organic phase.

The reaction conditions are not critical but are selected primarily on the basis of the properties of the reactants employed in the synthesis concerned, and also on the basis of practicality. For example, it may be mentioned that it is usually convenient to use a reaction temperature in the range of 25–75° C. and, in the case of water-rich medium, the pH is usually in the range 4–8.

The reaction temperature may also be varied to influence product yield and the activity and stability of the enzyme and does not restrict the scope of the invention. The temperatures most frequently used lie in the range 4–75° C., but lower temperatures and temperatures below 0° C. can be used which can be facilitated if organic cosolvent is used. An advantage with high temperatures is, for example, that high substrate concentrations may be used, which reduces the water activity and thus increases the yield of product. Another advantage is that the activity of the enzyme increases, which means shorter reaction times at increased temperatures. The upper temperature limit is determined by the thermostability of the enzyme and substrate in the specific reaction medium. In some reactions the thermostability of the enzyme is increased by the use of high sugar substrate concentration. High concentration of substrate e.g. cellobiose (>15% w/w) can be achieved by dissolving in hot buffered water followed by cooling to the desired reaction temperature.

The concentration of the acceptor is a parameter which can be used to influence the yield of the reactions according to the invention. High concentrations are usually preferable in both equilibrium and transglycosylation reactions to minimize hydrolytic side-reactions, which usually means that depending on the solubility of the acceptor, ca. 0.05–7 M concentration of acceptor is used. In general, high concentrations of substrates are obtained by heating the reaction mixture to near the boiling point for a few minutes, allowing the solution to cool to the reaction temperature (usually 4–75° C., depending on the temperature for optimum yield and thermostability of the enzyme/substrate) followed by addition of the enzyme. Cosolvents can be used to increase the solubility of substrates with hydrophobic groups.

The concentration of glycosyl donor in the reaction mixture is selected with regard to the Glcβ1-4GlcN derivative to be synthesized and also with regard to the properties of the enzyme and therefore do not restrict the use of the invention. In some cases, addition of the donor in small portions may be advantageous in order to minimize the risk that the donor also acts as an acceptor (unless this is desired). Cellobiose is generally used as the donor since it is a cheap substrate. The weight ratio of donor to acceptor is preferably ≧1:1 though the acceptor can be in excess.

The enzyme may be used in situ or after partial or complete purification from its natural environment. The enzyme may be isolated before use by e.g. homogenization, precipitation and/or chromatography (e.g. based on ion-exchange, affinity, size). The enzyme may be present in e.g. soluble, immobilized, cross-linked, crystalline form, may be used as modified with organic molecules like polyethylene glycol (PEG employing e.g. tresyl or tosyl activated PEG for covalent modification) or can be enclosed within micelles. Generally, the glycosidase can be used in vivo or in vitro in a more or less purified form and in different cell types (as cloned into a suitable cell type). The enzyme may be produced with recombinant techniques. Then, if desired, one or more of the amino acids in the amino acid sequence of the enzyme may be changed in order to optimize the properties of the enzyme, e.g. thermostability, catalytic efficiency and/ or stability in organic solvents. Variants of the glycosidase produced with recombinant technology which have at least 70% homology with the peptide chain of the natural variant are, together with the naturally occurring glycosidase, also useful according to the invention.

The synthetic reaction can be carried out with enzyme in vivo, that is under fermentation conditions with intact yeast cells and with cellobiose and acceptor in concentrations, for example, in the range 0.5 to 25% weight/volume. An excess of cellobiose is useful in some cases to improve the gluco-sylation of the acceptor and/or to prepare trisaccharides of the type mentioned above. This and other fermentation conditions with the necessary nutritional media/salts are easily determined by a person skilled in the art and does not limit the scope of the invention.

As glycosyl donor, cellobiose may be used or a β-glycoside of glucose such as an alkyl or aromatic glycoside (e.g. nitrophenyl β-glucoside).

Isolation of the product may be carried out in one or more steps involving one or more of the following procedures: extraction, chromatography (common solid supports that can be applied are e.g. Sephadex$^R$, silica, reversed-phase silica, charcoal, charcoal-celite), precipitation.

Depending on if intact yeast cells (fermentation conditions) or if crude, partially isolated or isolated or modified enzyme are used and also with regard to the solubility and stability of substrates, the reaction may be carried out at different conditions and preferably under conditions most suitable for the particular reaction. Such conditions are chosen by the person skilled in the art and do not limit the scope of the invention. Conventional pH (e.g. 4–8 obtained by e.g. acetate or phosphate buffer) and at low temperature, room temperature or at increased temperatures (e.g. in the range 0–50° C.) may be use if for example a crude, partially isolated, or isolated enzyme preparation is employed.

The reaction can be carried out in the presence of inert organic cosolvents in order to increase the solubility of the acceptor (e.g. hydrophobic acceptor) or to avoid hydrolysis reactions. If organic cosolvents (e.g. acetone, acetonitrile, tetrahydrofurane) are used together with buffered water as solvent for the reactions, lower temperatures than 0° C. (e.g. 30° C.) may be chosen in certain cases. The concentration of substrates are then usually in the range of 30 mM-7 M.

The enzyme may be used in soluble form or may be immobilized by e.g. adsorption, encapsulation, chelation, precipitation or covalent binding to a solid support, such as a polymeric substance, or a derivative thereof which is insoluble in protic or aprotic solvents (see for example Methods in Enzymology, vol. 135, Academic Press). The form selected is not critical to the invention. If the enzyme is used in soluble form, it may if desired first have been chemically modified in a suitable manner in order to e.g. increase the thermostability or the stability in organic cosolvents. Enzyme immobilized to an insoluble polymer comprising, for example, agarose, cellulose, hydroxyethyl acrylate, glass, silica, polyacrylic amide, polyacrlyate-based plastics, etc., is readily separated from the product mixture, and the enzyme may thus be reused.

Examples of immobilization are adsorption or covalent binding of the enzyme to a suitable solid phase such as glass, celite, silica, polysaccharides (e.g. cellulose, agarose), or plastics (e.g. polystyrene), activated with a suitable reactive group for covalent binding of the enzyme as is known in the art (see e.g. Methods in Enzymology, volumes 44, 104 and 135).

If intact yeast cells are used, the reaction conditions are chosen by the person skilled in the art and do not limit the scope of the invention. Preferable conditions are normally pH 4–7, 20–35° C. in buffered water containing nutrients for the yeast cells and substrates as exemplified in the non-limiting examples below.

Microorganisms which produce enzymes with the same structure or of a similar structure (e.g., containing similar three dimensional tertiary structure and active site structure) as the one from *Bullera singularis* can also be used.

If high concentrations of cellobiose are used, a considerable amount of glucose will be formed when a crude, partially purified or isolated enzyme is used (under fermentation conditions with intact yeast cells the yeast will consume a large amount of the formed glucose). The formed glucose will compete with the acceptor (and with water) for the glucosyl-enzyme intermediate, thus inhibiting the synthesis of product. A second enzyme which specifically removes glucose may thus be used during the reaction according to the invention, such as an isomerase (e.g. glucose isomerase) or an oxidase or dehydrogenase. Also, the product may be removed by the use of another specific enzyme, such as transferase or sulfatase which specifically converts the product to another desired product, thereby minimizing secondary hydrolysis of product and/or avoiding the need for isolation of the product prior to its use in further synthesis (see e.g. Enzyme Nomenclature, IUPAC-rules, 1984, Academeic Press for definitions of enzymes).

In a specific embodiment of the invention, the product can be used for chemical synthesis or further enzymatic synthesis with glycosidases or glycosyltransferases or other suitable enzymes such as oxidase, transsialidase or sulphatase.

The products obtained with the method according to the invention may be used directly for biological applications or may be used for further synthesis to obtain various Glc$\beta$1-4GlcN or GlcA$\beta$1-4GlcN group containing products employing enzymatic and/or chemical methods (see e.g. Example 5 below) of interest for e.g. various clinical, diagnostic, downstream processing or for food supplement purposes. For references to chemical modification of glucosamine and examples of possible chemical conversions of modified Glc$\beta$1-4GlcN structures see e.g. Binkley: Modern Carbohydrate Chemistry, Marcel Dekker, 1988 with references; Paulsen, Chem. Soc. Rev. 13, pages 15–45; Khan and Hindsgaul in Molecular Glycobiology, pages 206–229, Fukuda and Hindsgaul Editors, IRL Press, Oxford. For a reference to the use of thioethyl glycosides in the synthesis of various glycosides or for use as glycosyl donors in convergent block synthesis of tri-, tetra- and larger saccharides, see e.g. references cited in the Khan and Hindsgaul article.

The product obtained according to the invention may also be converted by enzymatic methods using e.g. lipases, sulfatases, glycosyltransferases, transsialidases and oxidases. In this way hydroxyl groups of the glucosyl or glucosaminyl moiety may be selectively modified with e.g. acyl groups, sulphate groups, carboxy groups, saccharide groups and other organic groups respectively, thus further extending the utility of the method of the invention for preparation of different derivatives and higher saccharides containing the Glc$\beta$1-4GlcN or GlcA$\beta$1-4GlcN group. Specific examples are the selection of a suitable derivative prepared by the method according to the invention for reaction with e.g. a sulfatase to obtain e.g. a 3'-O-sulphated derivative containing the Glc$\beta$1-4GlcN group. For references to enzymatic modifications, see e.g. Khan and Hindsgaul above (glycosyltransferases) and Wong and Whitesides in Enzymes in Synthetic Organic Chemistry, Pergamon (1994), Elsevier Science Ltd.; see also Enzyme Nomenclature, Academic Press (1984).

The aglycon of the Glc$\beta$1-4GlcN or GlcA$\beta$1-4GlcN containing product obtained according to the invention may not only be used in glycosylation reactions (for formation of other glycosides or for synthesis of oligosaccharides containing the above sequence) but may also be used for covalent binding to another molecule such as a protein, bead or a solid support and the resulting product may then be used for various purposes. Thus, nitrophenyl glycosides are for example useful after reduction to aminophenyl glycoside for covalent binding to various proteins or solid supports, which then may be used in diagnostic reagents, in down stream processing for separation of various proteins and enzymes including glycosyltransferases with specificity of various proteins and enzymes including glycosyltransferases with specificity of acceptors containing the Glc$\beta$1-4GlcNAc sequence or for solid phase synthesis of oligosaccharides (see e.g. Wong et al., J. Org. Chem. (1982), pages 5416–5418) and Wong and Whitesides, Enzymes in Syntheticd Organic Chemistry, Pergamon, 1994, for references to solid phase synthesis of oligosaccharides).

The following examples are illustrative of the invention:

Typically, the reactions were carried out in a fermentation reaction or with intact yeast cells obtained after fermentation, centrifugation, washing with buffer (50 mM sodium phosphate buffer, pH 6) and centrifugation, or with a partially purified enzyme preparation (obtained after desintegration of yeast cells under high pressure (e.g., 600 bar) and centrifugation of the solid material which was then used for synthesis).

EXAMPLE 1

Synthesis of Glcβ1-4GlcNPhtβSEt (Compound I) (SEt=$SCH_2CH_3$ group):

The initial concentrations of cellobiose (glycosyl donor) and GlcNPhtβ-SEt (acceptor; compound II) were 8 and 1.2% (w/v), respectively. Yeast cells (*Bullera singularis*) were added (10% w/v) and the reaction was carried out at 30° C. with moderate shaking (150 rpm) at pH 5.5 for five hours. Pure product (150 mg isolated from 1.3 g of Compound II) was obtained by Sephadex G10 chromatography and evaporation. The product was identified by NMR (400 MHz, Jeol) and the linkage positions determined with standard procedures.

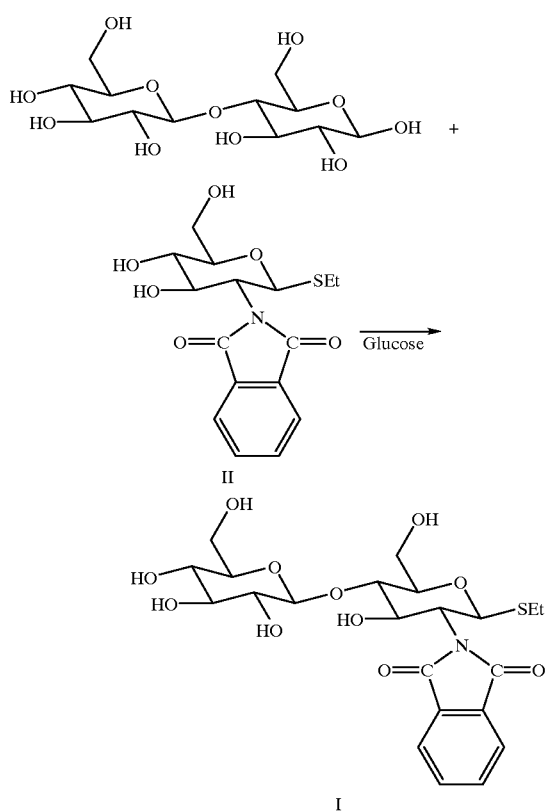

EXAMPLE 2

Synthesis of Glcβ1-4GlcNPhtβ-OH (Compound III):

The initial concentrations of cellobiose (glycosyl donor) and GlcNPhtβ-OH (acceptor; compound IV) were 8 and 4% (w/v), respectively. Yeast cells (*Bullera singularis*) were added (7.5% w/v) and the reaction was carried out at 30° C. with moderate shaking (150 rpm) at pH 5.5 for four hours. Pure product (400 mg isolated from 4 g of Compound IV) was obtained by Sephadex G10 chromatography followed by reversed phase (C18) column chromatography and evaporation. The product was identified by NMR (400 MHz, Jeol) and the linkage positions determined with standard procedures.

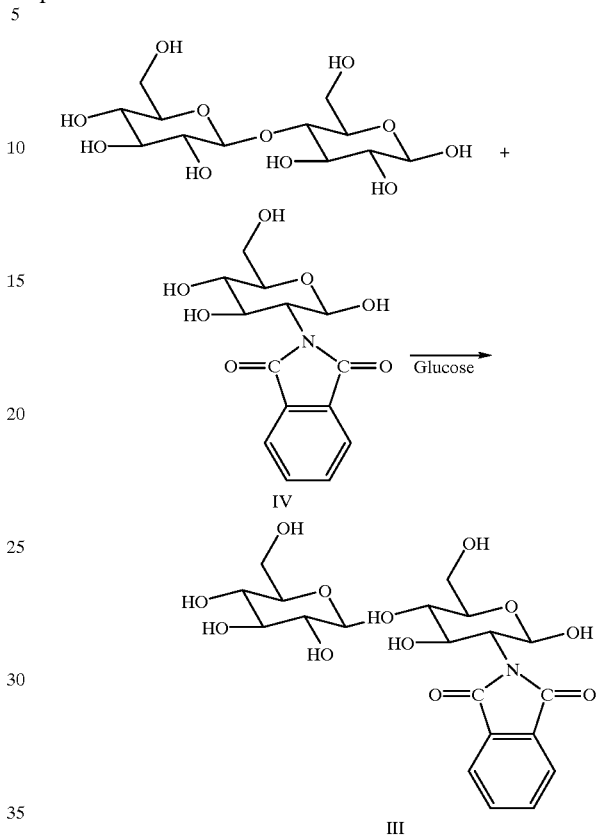

EXAMPLE 3

Synthesis of Glcβ1-4GlcN₃β-OMe (Compound V; $N_3$-azido group):

The initial concentrations of cellobiose (glycosyl donor) and GlcN₃β-OMe (acceptor; compound VI) were 8 and 4% (w/v), respectively. Yeast cells (*Bullera singularis*) were added (10% w/v) and the reaction was carried out at 30° C. with moderate shaking (150 rpm) at pH 5.5 for 30 hours. Pure product (50 mg isolated from 360 mg of Compound VI) was obtained by Sephadex G10 chromatography followed by reversed phase (C18) column chromatography and evaporation. The product was identified by NMR (400 MHz, Jeol) and the linkage positions determined with standard procedures.

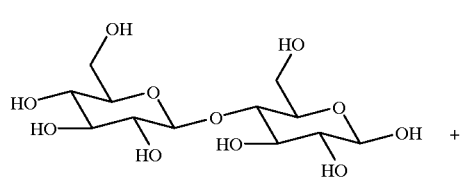

-continued

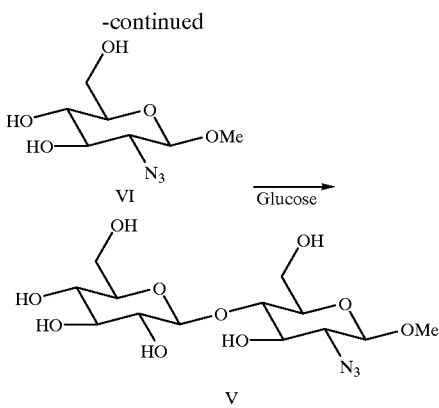

EXAMPLE 4

Synthesis of Glcβ1-4GlcNAcβ-SEt-(Compound VIII):

Glcβ1-4GlcNAcβ-SEt (Compound VIII) can be prepared in a manner analogous to Examples 1–3 using cellobiose (glycosyl donor) and GlcNAcβ-SEt (acceptor; compound VII).

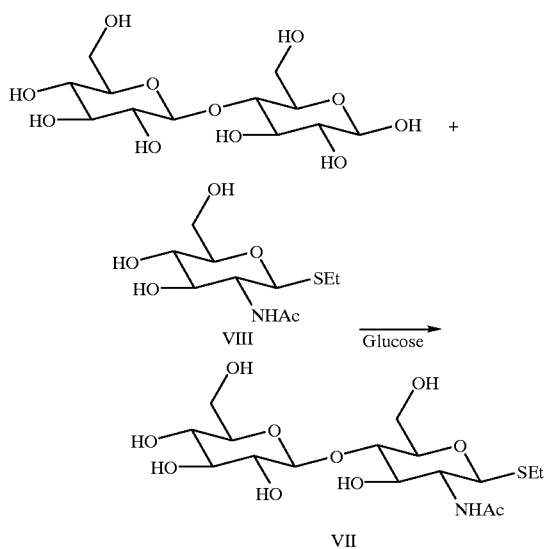

The acceptor substance in Examples 1–2 were prepared by standard chemical techniques known to the person skilled in the art from 2-amino-2-deoxy-D-glucosamine (GlcNH$_2$) via the peracetylated phthalimido derivative (peracetylated GlcNPht). The azido acceptor substrate in Example 3 was prepared from glucose via the glucal followed by azidonitration according to standard chemical techniques known to the person skilled in the art.

The compounds prepared above are of interest for use either for direct use in biological application or for synthesis of other Glcβ1-4GlcN or Glcβ1-4GlcN containing derivatives, higher oligosaccharides (R1=saccharide; R2 may be H2, acetyl or other group: other R are OH), and/or for conjugation to other type of molecules including proteins, antibodies, peptides, amino acids and enzymes (R1=protein, antibody, peptide, amino acid, modified amino acid, or enzyme glycosidically bound to the Glcβ1-4GlcN or GlcAβ1-4GlcN sequence).

EXAMPLE 5

Synthesis of product:

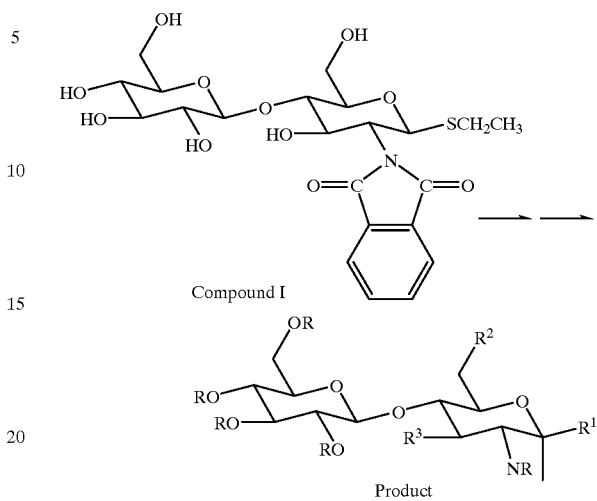

Peracylation or other modification of compound I, III or V with standard chemical techniques gives after isolation a protected compound with a free 3-OH group in the glucosamine part. Such a modified compound can be used for production of the Glc analog of e.g. Lewis-x compounds (Lewis-x =Galβ1-4(Fucα1-3)GlcNAc; R$^3$ in the figure above is an α-linked fucopyranosyl group; R$^2$ is an acetyl group and RO groups are HO-groups) and derivatives as well as other compounds modified in the 2-N group, 3-OH group (R$^3$=other sugar than L-fucose, e.g. instead of α-fucopyranosyl the 3-OH position can be modified with another sugar, mannose, galactose, etc. bound in α- or β-configuration or with another group), and/or, in the anomeric position of the glucosamino-residue the thioethyl disaccharides are routinely used for synthesis of other disaccharide glycosides such as amino acid glycosides (R$^1$= amino acid) or as a glycosyl donor with acceptor saccharides for convergent block synthesis of tri- or higher oligosaccharides.

Thus, for chemical preparation of the Glc analogs of Lewis-x and derivatives thereof Compound I, III or V can first be partially modified in the hydroxyl groups via e.g. peracetylation (pyridine+acetic anhydride). This gives after separation from other products the peracetylated compound I, III or V with a free 3-hydroxyl group and a -SEt, -OMe or OAc group, respectively, in R$^1$. The resulting compound can then be reacted with a fucopyranosyl compound (e.g. peracetylated L-fucopyranose) to give a Lewis-x derivative. After removal of the R groups and other protection groups and acetylation of the NH$_2$-group Glcβ1-4(Furα1-3) GlcNAc (Lewis-x) is obtained.

More specifically, the thioethyl group of Compound I (Glcβ1-4GlcNPhtβ-SEt), or preferably the peracetylated Compound I (IB), can be converted to peracetylated Glcβ1-4GlcNPhtβOR$^1$ or Glcβ1-4GlcNPhtβSR$^1$ where R$^1$ is an organic compound including a mono-, di- or higher oligosaccharide. The N-phthalimido group may be removed by standard techniques known in the art (e.g. hydrazine) and the NH$_2$ group formed may be used for conversion to, for example, Glcβ1-4GlcNC(O)R where R is methyl, ethyl or other organic group (see definition of NR" above), or Glcβ1-4GlcNR where R is an inorganic group (e.g. sulfate) or a compound containing an organic group (aliphatic and/or aromatic).

Compound I can be e.g. peracetylated (pyridine+acetic anhydride) to form a compound (IB) of the type below:

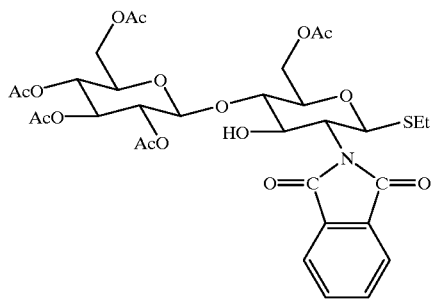

Compound IB can be reacted with e.g. peracylated L-fucopyranose to form Compound IC:

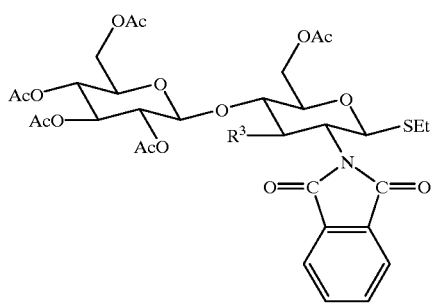

Another modified form of IB, L-fuc or another sugar than fucose might be selected to give other compounds or higher yields.

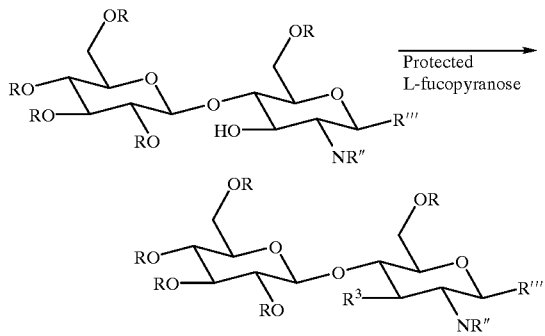

Other types of protection groups may be selected by the person skilled in the art to achieve higher yields.

The acetyl groups and phthalimido group of Compound IC can be removed by standard techniques and the $NH_2$ group acetylated to form Compound ID (Glcβ1-4(Fucα1-3)GlcNAcβSEt; thioethyl glycoside of Lewis-x); SEt can also be removed to form Compound IE (Glcβ1-4(Fucα1-3)GlcNAc; Lewis-x).

The phthalimido group of Compound IC can be removed and the $NH_2$ group coupled to R-X and/or the -SEt group is used for coupling to sugar or hydroxyl group containing compound $R^1OH$ to form Compound IF (Glcβ1-4(Fucα1-3)GlcNR-$R^1$; a derivative of Lewis-x where R is an inorganic or organic group and $R^1$ is a sugar, —OH, or organic group including amino acids or peptides.

The above derivatives can then be converted to other derivatives (e.g. by chemical modification of R" and/or R''' groups as described above, or by further enzymatic reactions). The above derivatives may be used in the various types of applications described above as appropriate. Examples are in clinical, diagnostic, downstream processing applications.

The OH group (e.g., 6-OH) of the glycosyl group of the Glcβ1-4GlcN derivatives can be specifically oxidized to form, for example, the following compounds (where A is the OH group oxidized to COOH):

(i) oxidize Glcβ1-4GlcNPhtβ-SEt (Compound I) (SEt= $SCH_2Ch_3$ group) to form GlcAβ1-4GlcNPhtβ-SEt;

(ii) oxidize Glcβ1-4GlcNPhtβ-OH (Compound III) to form GlcAβ1-4GlcNPhtβ-OH;

(iii) oxidize Glcβ1-4GlcN$_3$β-OMe (Compound V; $N_3$=azido group) to form GlcAβ1-4GlcN$_3$β-OMe; and (iv) oxidize Glcβ1-4GlcNAcβ-SEt (Compound VIII) to form GlcAβ1-4GlcNAcβ-SEt.

In the chemical oxidation of (i) and (iv) above, it is preferable to substitute the SEt with an R group where R is an aglycon for greater stability.

Oxidation may occur through chemical or enzymatic (e.g., oxidase) methods, e.g. for conversion of one or several OH-groups to carboxyl groups. Several oxidizing reagents are known from the literature. For example, nitroxyl mediated oxidation which is highly selective for primary hydroxyl groups of glucosides (see e.g., de Nooy et al., Carbohydrate Research (1995), volume 269, pages 89–98, incorporated by reference in its entirety). This reaction is used to convert 6-OH groups of glucosides to a 6-COOH group, thus forming glucuronic acid derivatives (GlcAβ-).

Enzymatic methods relying on oxidoreductases (E.C. 1.1) are also frequently used for specific oxidation (see e.g. Enzyme Nomenclature, Academic Press, 1984) of primary hydroxyl groups to carboxyl groups. See also Wong and Whitesides, Enzymes in Syntheticd Organic Chemistry, Pegamon, 1994.

The above type of reactions may be used by those skilled in the art for conversion of the products obtained by the method according to the present invention, for example to the corresponding 6'-COOH derivatives (e.g., GlcAβ1-4GlcNAcβ-SEt). Such oxidation may also be carried out after conversion of e.g. products I, III, or V to other derivatives, thus extending the flexibility of the method.

Chemical and/or enzymatic oxidation of the 6-OH group of the glucosyl unit to a 6-COOH group leads to formation of products containing the GlcAβ1-4GlcN structure present in glycosaminoglycans, such as heparin. Thus, three examples of GlcAβ1-4GlcN containing products obtained with the method according to the present invention are shown below as obtained via oxidation of the 6-OH group of the above illustrated GlcAβ1-4GlcN containing products:

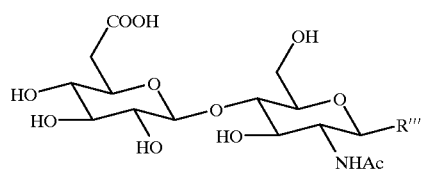

Abbreviation:
GlcAβ1-4GlcNAc-R'''

-continued

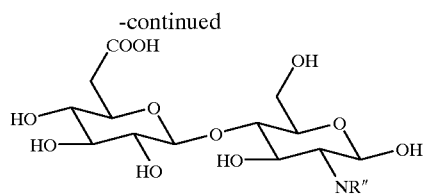

Abbreviation:
GlcAβ1-4GlcNR''-R'''

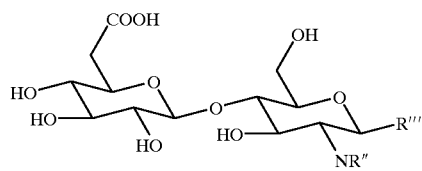

Abbreviation:
GlcAβ1-4GlcNR''-R'''

These types of compounds (e.g., GlcAβ1-4GlcNPhtβ-SEt; GlcAβ1-4GlcNPhtβ-OH; GlcAβ1-4GlcNβ-OMe; and GlcAβ1-4GlcNAcβ-SEt) are of interest e.g. for the preparation of the heparin-derived fragments of the type GlcAβ1-4GlcNSO$_3$H-R and GlcAβ1-4GlcNAc-R. In addition to being useful for preparation of heparin fragments, the target molecule is also of interest for preparation of shorter active structures. Thus, uncharged disaccharides of the latter type have recently been shown to specifically bind to heparin binding fibroblast growth factors, indicating that di- or tri-saccharide derivatives of high biological activity can be developed (see e.g. Science (1995), volume 268, pages 432–435, incorporated by reference in its entirety).

The Pht, N$_3$ and SEt groups above are useful for conversion to a broad range of other substituents (and, thus fragments and derivatives of heparin derived compounds) and alternatively, the oxidations above may be carried out after any desired conversions of the intermediate products above have been carried out, thus introducing further flexibility and opportunities.

Further variations and modifications of the foregoing will be apparent to those skilled in the art and such variations and modifications are attended to be encompassed by the claims that are appended hereto.

Swedish Application 94 000346 filed on Jan. 6, 1994 and the PCT application filed on Jan. 9, 1995 (PCT publication WO95/18864) are relied on and incorporated by reference.

What is claimed:

1. A method of producing a Glcβ1-4GlcN derivative with β1-4 linkage, said method comprising
   (1) reacting
   (a) at least one donor substance GlcβOR where R is an organic group, and
   (b) at least one acceptor substance which is a glucopyranosamino derivative having the formula GlcNR''-R''',
   wherein NR'' is an azido, 2-N-acetyl-, 2-N-phtalimido, or another compound containing an inorganic and/or organic group bound to the 2-N-group of glucosamine,
   wherein R''' is a glycosidically bound fluoro or is an O-, C-, N- or S-glycosidically bound aliphatic or aromatic compound,
   (c) in the presence of *Bullera singularis* or a composition or lysate of *Bullera singularis* to form said Glcβ1-4GlcN derivative; and
   (2) optionally isolating said Glcβ1-4GlcN derivative.

2. The method according to claim 1, wherein said organic group in said donor substance GlcβOR is selected from the group consisting of a sugar, a lower alkyl group, and an aromatic group.

3. The method according to claim 2, wherein said sugar is glucose, wherein said lower alkyl group is methyl or ethyl, and wherein said aromatic group is phenyl or nitrophenyl.

4. The method according to claim 3, wherein said sugar is glucose and wherein said aromatic group is nitrophenyl.

5. The method according to claim 1, wherein said R''' is a lower alkoxy, lower thioalkyl, thioaromatic, -OEtBr or nitrophenoxy.

6. The method according to claim 5, wherein said lower alkoxy is methyloxy or ethyloxy, wherein said lower thioalkyl is β-linked thioethyl, and wherein said thioaromatic is thiophenyl.

7. The method according to claim 1, wherein said NR'' is N-phthalimido, NH—C(O)—R, NHR or NRR' where R and R' are a group containing an organic and/or an inorganic group.

8. The method according to claim 7, wherein R and R' are a group containing an aliphatic and/or aromatic group.

9. The method according to claim 8, wherein said aliphatic group is a alkyl, alkoxy, or allyloxy and wherein said aromatic group is phenyl, benzyl or phenyloxy.

10. The method according to claim 9, wherein said lower alkyl is methyl, ethyl or propyl and said lower alkoxy is methoxy or ethoxy.

11. The method according to claim 1, wherein said NR'' is N-phthalimido, azido or N-acetyl.

12. The method according to claim 1, wherein said Glcβ1-4GlcN derivative is Glcβ1-4GlcNPhtβ-SEt, Glcβ1-4GlcNPhtβ-OMe, Glcβ1-4GlcNPht, Glcβ1-4GlcN$_3$β-OMe, Glcβ1-4GlcNAcβ-SEt, or Glcβ1-4GlcNAcβ-OPhNO$_2$-p.

13. The method according to claim 1, wherein said method further comprises adding a second enzyme which specifically removes glucose.

14. The method according to claim 13, wherein said second enzyme is an isomerase or an oxidase.

15. The method according to claim 14, wherein said isomerase is glucose isomerase.

16. The method according to claim 1, wherein said step (c) utilizes an E.C. group 3.2 glycosidase obtained from *Bullera singularis*.

17. The method according to claim 1, wherein said step (c) utilizes a soluble or immobilized preparation containing crude, partially isolated or isolated β-glycosidase from *Bullera singularis*.

18. The method according to claim 16 wherein said glycosidase is immobilized via precipitation, adsorption, enclosure, chelation, or covalent bonding, to a polymeric substance or derivative thereof which is insoluble in protic or aprotic solvents.

19. The method according to claim 18, wherein said polymeric substance is a polysaccharide, a plastic, or a glass, and which has been activated and contains reactive groups selected from the group consisting of cyanate, organic sulphonates, aldehyde, diazonium, epoxy, divinylsulphone, and triazine groups.

20. The method according to claim 19, wherein said polysaccharide is cellulose or agarose and said plastic is polyacrylamide, polyvinylalcohol, or polystyrene.

21. A method for the production of the glucosyl analog of Lexis-x and derivatives thereof, said method comprising peracetylating the Glcβ1-4GlcN derivative produced by the method according to claim 1 to form a peracetlyated compound, reacting said peracetlyated compound with a fucopyranosyl compound and subsequently removing the R groups and acetylating the $NH_2$ group.

22. The method according to claim 21, wherein the R groups are acetyl and phthalimido.

23. The method according to claim 1 wherein in (b) if NR" is NHAc then R'" is not OH and if NR" is not NHAc then R'" may be OH.

24. A method for the production of a di-, tri-, or higher oligosaccharide containing compound which contains at least one GlcAβ1-4GlcN structural unit, comprising oxidizing at least one OH group of the glycosyl group of the Glcβ1-4GlcN derivative produced according to the method of claim 21.

* * * * *